United States Patent [19]

Scholl

[11] Patent Number: 4,935,534
[45] Date of Patent: Jun. 19, 1990

[54] 1-(N-FORMYLAMINO)-2,4-DICYANOBUTANE AND A PROCESS FOR ITS PRODUCTION

[75] Inventor: Hans-Joachim Scholl, Cologne, Fed. Rep. of Germany

[73] Assignee: Bayer Aktiengesellschaft, Bayerwerk, Fed. Rep. of Germany

[21] Appl. No.: 327,079

[22] Filed: Mar. 22, 1989

[30] Foreign Application Priority Data

Mar. 31, 1988 [DE] Fed. Rep. of Germany ....... 3810973

[51] Int. Cl.$^5$ .......................................... C07C 121/43
[52] U.S. Cl. .................................................. 558/445
[58] Field of Search ........................................ 558/445

[56] References Cited

U.S. PATENT DOCUMENTS 4,701,546 10/1987 Bewert et al. ...................... 558/445
4,845,261  7/1989 Fuentes ................................ 558/101

OTHER PUBLICATIONS

*Handbook of Chemistry and Physics* 1975, CRC Press, pp. D-127 and D-128.
Hölfe, Steglich, and Vorbrüggen, Angew, Chem. Int. Ed. Engl. 17, 569–583, (1978).
J. Biol. Chem., 251, 2263–2270 (1976)-(Chem. Abstract Attached).

*Primary Examiner*—Joseph Paul Brust
*Assistant Examiner*—MarySue Howard
*Attorney, Agent, or Firm*—Joseph C. Gil; Richard E. L. Henderson

[57] ABSTRACT

This invention relates to the novel compound 1-(N-formylamino)-2,4-dicyanobutane, which is useful as an intermediate, for example, in the preparation of -aminomethyl glutamic acid. This invention further relates to a process for the production of 1-(N-formylamino)-2,4-dicyanobutane by the reaction of 2,4-dicyano-1-butene and formamide in the presence of 4-aminopyridine derivative.

8 Claims, No Drawings

1-(N-FORMYLAMINO)-2,4-DICYANOBUTANE AND A PROCESS FOR ITS PRODUCTION

BACKGROUND OF THE INVENTION

This invention relates to the novel chemical compound 1-(N-formylamino)-2,4-dicyanobutane and to a process for its production from 2,4-dicyano-1-butene and formamide.

SUMMARY OF THE INVENTION

A new chemical compound has been found, namely 1-(N-formylamino)-2,4-dicyanobutane, which has the following formula

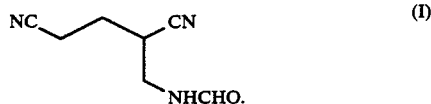

A process for the production of 1-(N-formylamino)-2,4-dicyanobutane has also been found and is characterized by the reaction of 2,4-dicyano-1-butene and formamide in the presence of a 4-aminopyridine derivative.

DETAILED DESCRIPTION OF THE INVENTION

In the process of this invention, suitable quantities of formamide include, for example, from 0.5 to 10 mol of formamide per mol of 2,4-dicyano-1-butene. The formamide is preferably used in a quantity of 1 to 6 mol per mol.

Suitable 4-aminopyridine derivatives serve as a catalytically active base and include, for example, compounds corresponding to the following formula

wherein $R^1$ and $R^2$ are independently $C_1$–$C_6$ alkyl, or $R^1$ and $R^2$ taken together are $C_3$–$C_5$ alkylene forming a ring with the 4-amino nitrogen atom.

The term "$C_1$–$C_6$ alkyl" refers to straight or branched chain aliphatic hydrocarbon groups having from 1 to 6 carbon atoms. Examples of $C_1$–$C_6$ alkyl are methyl, propyl, butyl, pentyl, hexyl, and the isomeric forms thereof.

The term "$C_3$–$C_5$ alkylene" refers to straight or branched chain aliphatic hydrocarbon groups having from 3 to 5 carbon atoms and bonded to the 4-amino nitrogen atom through two different carbon atoms so as to form a heterocyclic ring substituent on the pyridine ring. Examples of $C_3$–$C_5$ alkylene are propylene (forming an azetidino substituent), optionally substituted with one or two methyl groups or an ethyl group; butylene (forming a pyrrolidino substituent), optionally substituted with a methyl group: and pentylene (forming a piperidino substituent).

Preferred 4-aminopyridine derivatives are 4-(N,N-dimethylamino)pyridine and 4-pyrrolidinopyridine.

The quantity in which the catalytically active substituted 4-aminopyridine base is used is not critical. However, to obtain a sufficiently fast reaction, the catalytically active base is normally used in a quantity of 1 to 12 mol-% per mol of 2,4-dicyano-1-butene.

The process is preferably carried out in the absence of a solvent.

Suitable reaction temperatures are for example those in the range from 0° to 120° C. and preferably in the range from 20° to 100° C.

The reaction is preferably carried out at atmospheric pressure, although it may also be carried out at elevated pressure.

The process according to the invention does not require any special conditions for the reaction or the work-up. After separation of the lower-boiling constituents formamide and the catalyst (for example by distillation or thin-layer evaporation), 1-(N-formylamino)-2,4-dicyanobutane accumulates in the form of a faintly colored liquid. Normally this liquid is sufficiently pure for use as an intermediate without further purification.

1-(N-formylamino)-2,4-dicyanobutane is an important intermediate product. For example, it provides convenient access to the production of α-aminomethyl glutamic acid.

The following examples further illustrate details for the preparation of the compounds of this invention. The invention, which is set forth in the foregoing disclosure, is not to be construed or limited either in spirit or in scope by these examples. Those skilled in the art will readily understand that known variations of the conditions and processes of the following preparative procedures can be used. In the following examples, all percentages are percentages by weight and all temperatures are degrees Celsius unless otherwise noted.

DESCRIPTION OF THE PREFERRED EMBODIMENTS

EXAMPLE 1

4-(N,N-Dimethylamino)pyridine (7.4 g, 0.06 mol) is introduced with stirring at room temperature into a solution of 2,4-dicyano-1-butene (106 g, 1.0 mol) and formamide (90 g, 2.0 mol). The clear solution is stirred for 23 hours at 60° C. and freed from residual starting materials and catalyst components using thin-layer evaporation (145° C./0.1 mbar). The resulting light yellow, clear liquid thus obtained consists of 95% pure (GC analysis) 1-(N-formylamino)-2,4-dicyanobutane (I). Yield: 75 g (4? %); selectivity: 95%.

Analysis. Calcd. for $C_7H_9N_3O$: C, 55.6; H, 6.0; N, 27.8. Found: C, 56.0; H, 6.0: N, 27.4.

EXAMPLE 2

A solution of 2,4-dicyano-1-butene (430 g, 4.1 mol), formamide (548 g, 12.2 mol) and 4-(N,N-dimethylamino)pyridine (14.9 g, 0.12 mol) is reacted as in Example 1. The reaction product is worked up in the same way as in Example 1.

204 g of 98% pure (GC analysis) 1-(N-formylamino)-2,4-dicyanobutane (I) and 780 g of distillate are obtained. Yield: 204 g (32%): selectivity: 97%.

Analysis. Calcd. for $C_7H_9N_3O$: C, 55.6: H, 6.0; N, 27.8. Found: C, 55.8: H, 6.1: N, 27.5.

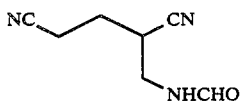

What is claimed is:

1. A process for the production of 1-(N-formylamino)-2,4-dicyanobutane comprising reacting 2,4-dicyano-1-butene and formamide in the presence of a 4-aminopyridine derivative having the structure

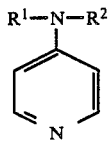

wherein $R^1$ and $R^2$ are independently $C_1$–$C_6$ alkyl, or $R^1$ and $R^2$ taken together are $C_3$–$C_5$ alkylene forming a ring with the 4-amino nitrogen atom.

2. A process according to claim 1 wherein the 4-aminopyridine derivative is 4-(N,N-dimethylamino)-pyridine.

3. A process according to claim 1 wherein the 4-aminopyridine derivative is 4-pyrrolidinopyridine.

4. A process according to claim 1 wherein about 0.5 to 10 mol of formamide per mol of 2,4-dicyano-1-butene are used.

5. A process according to claim 1 wherein about 1 to 6 mol of formamide per mol of 2,4-dicyano-1-butene are used.

6. A process according to claim 1 wherein about 1 to 12 mol-% of the 4-aminopyridine derivative per mol of 2,4-dicyano-1-butene is used.

7. A process according to claim 1 for the production of 1-(N-formylamino)-2,4-dicyanobutane comprising reacting 2,4-dicyano-1-butene and about 1 to 6 mol of formamide per mol of 2,4-dicyano-1-butene in the presence of about 1 to 12 mol-% of 4-(N,N-dimethylamino)-pyridine per mol of 2,4-dicyano-1-butene.

8. 1(N-formylamino)-2,4-dicyanobutane, having the formula